(12) United States Patent
Shao

(10) Patent No.: US 6,254,897 B1
(45) Date of Patent: Jul. 3, 2001

(54) HERBAL COMPOSITION FOR TREATMENT OF TINEA INFECTIONS AND METHOD OF MAKING SAME

(76) Inventor: Yong Fu Shao, 1215 Summit Rd., McLean, VA (US) 22101

( * ) Notice: Subject to any disclaimer, the term of this patent is extended or adjusted under 35 U.S.C. 154(b) by 0 days.

(21) Appl. No.: 09/658,886

(22) Filed: Sep. 11, 2000

(51) Int. Cl.⁷ ..................................................... A61K 35/78

(52) U.S. Cl. .......................... 424/725; 514/828; 514/858; 424/547

(58) Field of Search .................................... 424/725, 547, 424/195.1; 514/825, 858

(56) References Cited

FOREIGN PATENT DOCUMENTS

1214261  *  4/1999  (CH) .

* cited by examiner

*Primary Examiner*—Francisco Prats
*Assistant Examiner*—Kailash C. Srivastava

(57) ABSTRACT

The present invention relates to a novel herbal composition having antimycotic activity effective against tinea infections, comprising plant substances as main ingredients, and method of treating a patient having a tinea infection. More particularly, the present invention relates to an antimycotic composition effective against tinea infections utilizing natural substances obtained from a combination of *Angelicae Pubescentis Radix, Notopterygium Radix* and *Haliotis Diversicolor Reeve*, and in some embodiments further comprising *Pheretima Aspergillum* (Perrier).

34 Claims, 2 Drawing Sheets

HERBAL COMPOSITION FOR TREATMENT OF TINEA INFECTIONS AND METHOD OF MAKING SAME

BACKGROUND OF THE INVENTION

The present invention relates to a novel herbal composition having antimycotic activity effective against tinea infections comprising plant substances as main ingredients, a method of manufacture and method of treating a patient having a tinea infection. More particularly, the present invention relates to an antimycotic composition effective against tinea infections utilizing natural substances obtained from a combination of *Angelicae Pubescentis Radix, Notopterygium Radix* and *Haliotis Diversicolor Reeve*, and in some embodiments further comprising *Pheretima Aspergillum* (Perrier).

The body normally serves as host for a variety of bacteria and fungi. Most of the time, the balance between the body as host and the microorganisms is maintained. Sometimes, however, conditions exist that permit the microorganisms to tip that balance, causing an infection.

Certain fungal infections of the skin known as tinea infections are caused by dermatophytes, which are members of the Trichophyton, Microsporum and Epidermophyton species. These mold-like fungi thrive in warm, moist areas, thriving on the dead tissues of hair, nails, and outer skin layers. Tinea infections include tinea pedis, known as athlete's foot; tinea corporis, known as ringworm; tinea capitis which is a fungal infection of the scalp that can cause hair loss; tinea cruris known as jock itch or tinea of the groin; tinea unguum which is tinea of the nails; and tinea versicolor, a superficial fungal infection that produces brown, tan, or white spots on the trunk of the body. Tinea infections are contagious and can be passed through direct contact or by contact with clothing, from shower and pool surfaces, and even from pets.

Athlete's foot or tinea pedis is by far the most common form, with more than 900 million people in the world suffering from the disease. It presents with redness, itching, burning, cracking, scaling, swelling and occassionally bleeding. The nails may show thickening, pitting and subungal debris. Local antifungals include imidazoles, such as miconazole nitrate and clotrimazole, tolnaftate, and terbinafine hydrochloride. As the common fungicidal and fungistatic chemical treatments frequently fail to contact the fungi in the horny layers of the skin, athlete's foot seldom clears with local antifungal therapy and systemic antifungals, including terbinafine hydrochloride taken in tablet form, may be required to be taken for considerable lengths of time, potentially for months. Common treatments for athlete's foot using local antifungals require treatment two or three times a day for at least 10 to 14 days, and for some medications, for up to four weeks. It is common treatment to apply the topical antifungal for two weeks after the skin is healed, to eradicate all remaining fungal spores.

Reoccurrences of the infection are frequent, however. For some patients, such as those also afflicted with diabetes or circulatory problems, tinea infections and their treatment can be quite serious. Ringworm presents with lesions that are characterized by central clearing and fine peripheral scales. The lesions may be itchy. There may be deep inflammatory nodules. Systemic therapy is required in severe cases with widespread lesions. Systemic therapy almost always includes griseofulvin. Nausea and gastrointestinal disturbances are common side effects of the drug, but long term use may lead to hepatic or bone marrow failure.

Methods for reducing toxicity of treatments include use of herbal formulations rather than purified pharmaceuticals. Herbs have long been known and used throughout the world for treatment of many conditions, including skin conditions, and there is at least some evidence that herbal remedies may tend to have less deleterious side effects than corresponding pharmaceuticals.

Increasingly, herbal remedies are sought due to concerns caused by antibiotic-resistant and other drug-resistant infectious agents. Even with herbal treatments, however, numerous difficulties are encountered in the treatment of medical conditions. A single herb may contain numerous active, and sometimes conflicting, components. The common herb, rhubarb, for example, may be used in small doses for treating constipation due to its tannic acid component, but is a potent laxative in larger doses because of other components. Other herbs, however, such as black walnut extract which is used to treat athlete's foot, related fungal infections and cancers, as well as to lower blood pressure and cholesterol, can be toxic if taken inappropriately. Additional potential difficulties arise from plant-to-plant variation in the concentration and efficacy of active components. Such difficulties are considerably exacerbated with respect to herbal compositions. In addition to those difficulties mentioned in connection with single herbs, combinations raise the possibility of synergistic effects among components in the various herbs, and increase the difficulties associated with anticipating and analyzing side effects.

Many herbs are reported to have substantial effects on skin ailments. Herbs within this group include, for example *Angelicae Pubescentis Radix* for treatment of psoriasis. Herbs traditionally known or used for treating athlete's foot specifically, include tea tree, garlic, goldenseal and various parts of the black walnut tree, which is known to be toxic when taken inappropriately. Combinations of herbs are also known to have substantial effects on skin ailments. For example, one herbal treatment for tinea infections uses herbal extracts from Aloe vera, Chicory root, Catnip, St. John's wort, vitamins A and E, in a cream base. This treatment is recommended for application 3 to 4 times daily for 2 to 3 days after all lesions are healed and completely gone.

While many effects of individual herbs are known, it is often unclear in the art which herbs to combine, and in which percentages, to achieve improved results.

SUMMARY OF THE INVENTION

Figure 1:
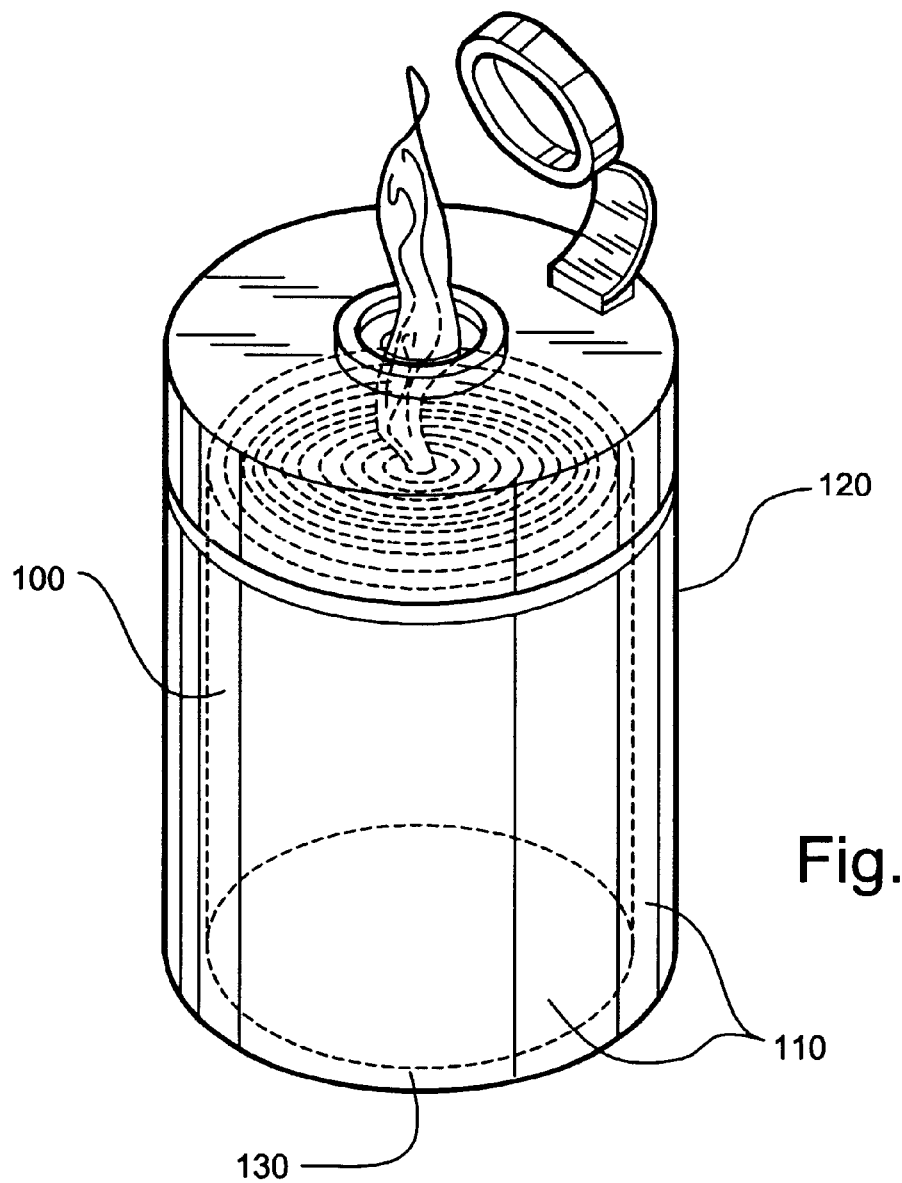
FIG. 1 depicts a container for example a wipe or a sponge for applying the composition of the instant invention to a body part.
Figure 4:
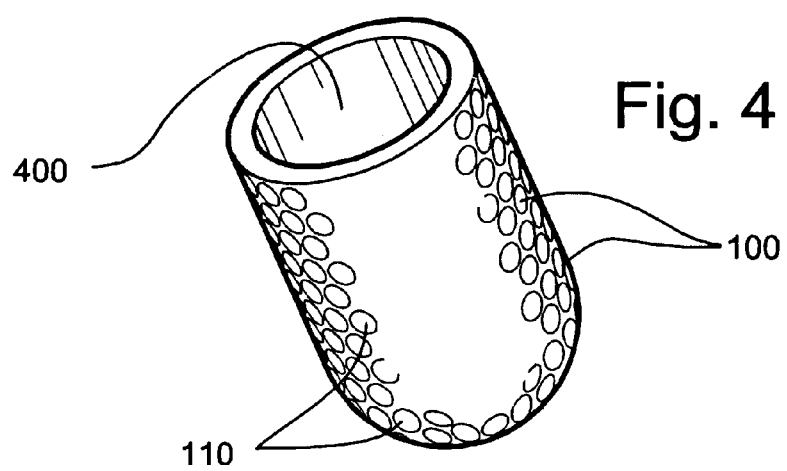
FIG. 4 depicts a container wherein the composition is lined, and such container can be worn on a toe.
Figure 2:
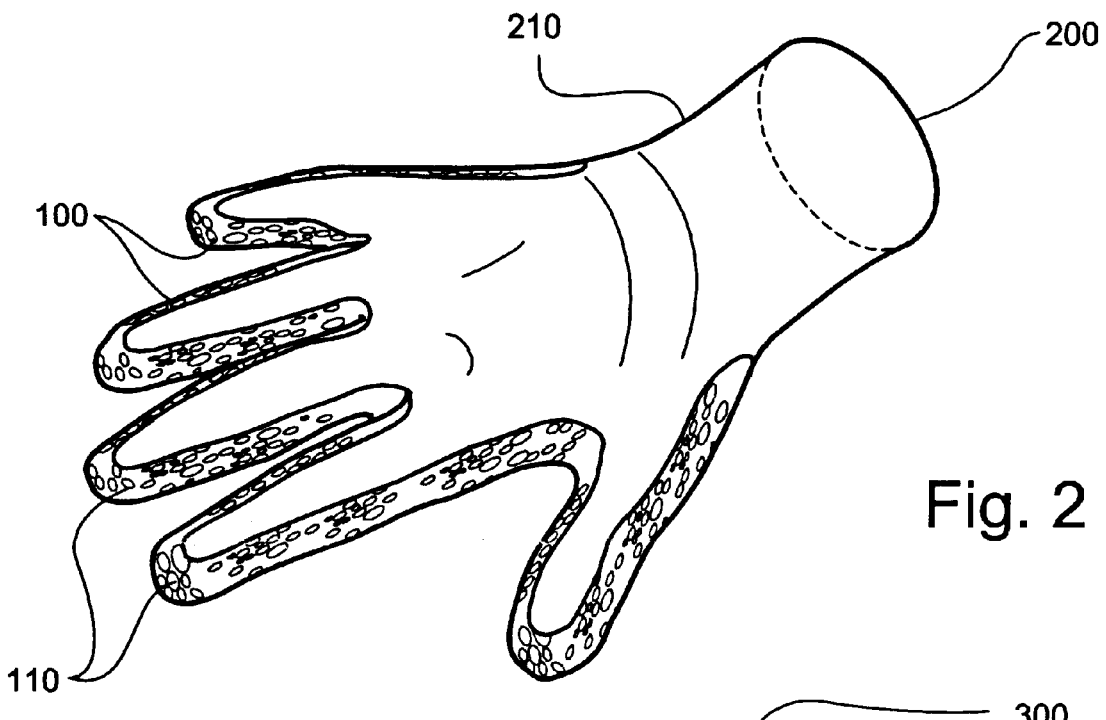
FIG. 2 depicts a glove wherein the composition of the present invention is contained as a layer.
Figure 3:
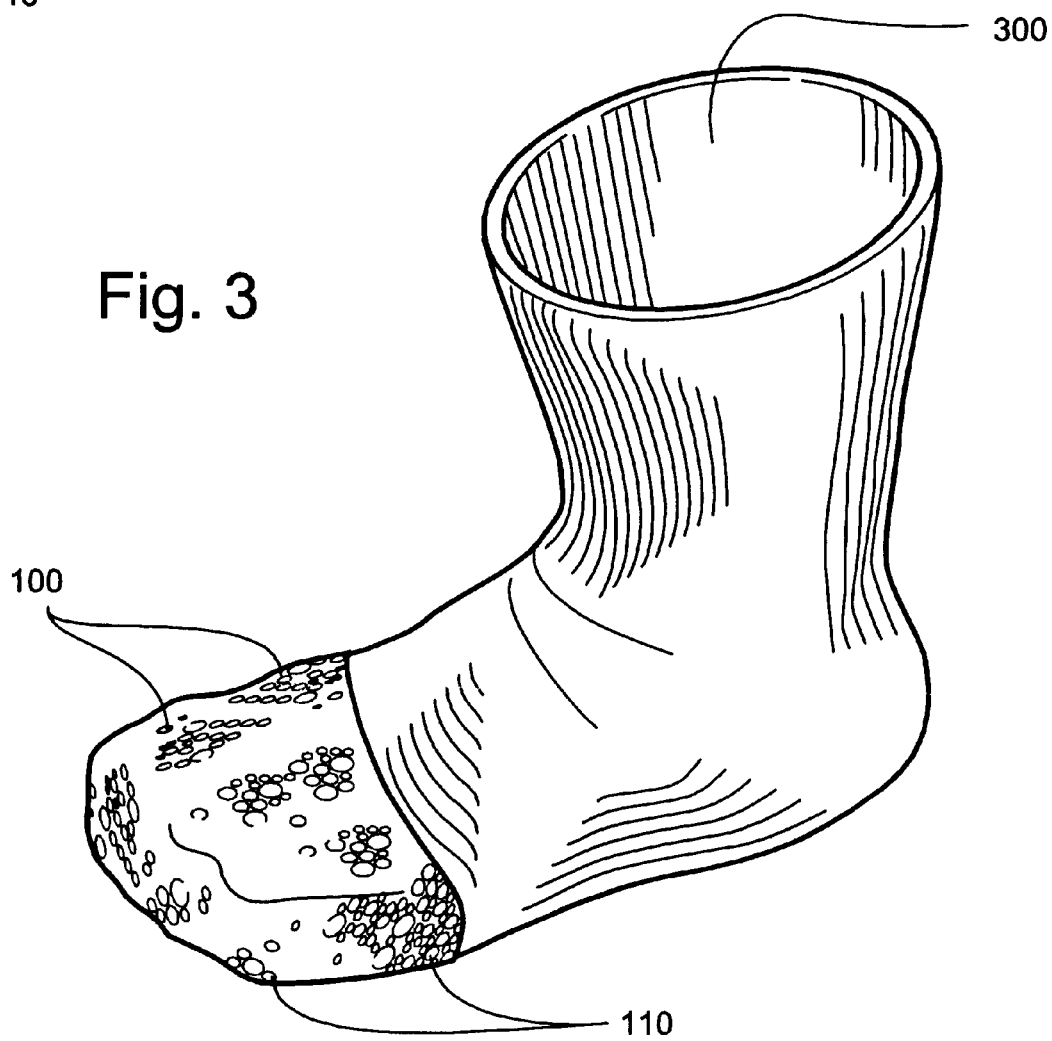
FIG. 3 depicts a sock wherein the composition of the present invention is contained as a layer.

Accordingly, it is an object of the present invention to provide a composition of natural substances for treatment of tinea infections.

Another object of the present invention to provide a composition of natural substances for treatment of tinea pedia infections.

A further object of the present invention to provide a convenient composition for treatment of tinea pedia infections.

Still another object of the present invention to provide a composition of natural substances for once-a-day treatment of tinea infections.

Yet another object of the present invention to provide a composition for treating tinea infections quickly and effectively.

A further object of the present invention to provide a composition for treating and diminishing reoccurrence of tinea pedia infections.

Other objects and further scope of applicability of the present invention will become apparent from the detailed description to follow. It should be understood, however, that the detailed description and specific examples, while indicating embodiments of the invention, are given by way of illustration only, since various changes and modifications within the spirit and scope of the invention will become apparent to those skilled in the art.

The present invention relates to An herbal composition comprising *Angelicae Pubescentis Radix, Notopterygium Radix* and *Haliotis Diversicolor Reeve* wherein each component is provided in an amount effective for the treatment of tinea infection, and further comprising vinegar or *Pheretima Aspergillum* (Perrier), products containing the herbal composition for treating a tinea infection, method of making the herbal composition, and method of treating a patient using the herbal composition.

DETAILED DESCRIPTION OF THE INVENTION

The present invention relates to An herbal composition comprising *Angelicae Pubescentis Radix, Notopterygium Radix* and *Haliotis Diversicolor Reeve* wherein each component is provided in an amount effective for the treatment of tinea infection. One composition of the present invention comprises the natural substance ingredients of the present invention in roughly equal parts by weight. Another embodiment of the present invention comprises *Angelicae Pubescentis Radix* in an amount approximately 30–40% (dry weight basis) of the combination; *Notopterygium Radix* in an amount approximately 17–25% (dry weight basis) of the combination; and *Haliotis Diversicolor Reeve* in an amount approximately 30–40% (dry weight basis) of the combination. Yet another embodiment of the invention further comprises *Pheretima Aspergillum*, known also as Perrier obtained from earthworms, in an amount approximately 17–25% (dry weight basis) of the combination.

*Angelicae Pubescentis Radix* is a member of the family Umbelliferae and is characterized by a root that is thick and fleshy, with a well-developed axial root and several branch roots in the lower part. The root generally grows to a length of 10 to 30 cm. The root top is generally enlarged, growing from 1 to 3 cm in diameter and containing annular rings, depressed stem scars and remnant leaf bases at the top. It is generally prepared by crosscutting. It tends to have a heavily fragrant odor, and causes numbing of the tongue when tasted. In traditional herbal treatments, it is considered bitter and acrid in taste, warm in nature and attributive to kidney and urinary bladder channels. Traditional uses of this herb include treatment of flaccidity and pale complexion, vertigo, palpitation, irregular menstruation, amenorhea, dysmenorrhea, carbuncle, celluliti, sore, ulcer, relieving constipation, relieving arthralgia, promoting sweating and for common cold with severe chills and lower fever. It is also used for toothache. Its pharmacological actions are known to include sedative, analgesic and antiphlogistic properties. Bergapten is an active component that is an ultraviolate absorbent. It is also known to contain coumarin which has antimycotic activity. It is generally prepared in thin slices of root by cleaning, slicing and drying. The root slices may be moistened with liquor and cauterized.

Both the Rhizome and root of *Notopterygium Radix* are used in traditional herbal treatments. The rhizome may be cylindrical and somewhat curved, tending to grow from 4 to 15 cm long and 0.6 to 3 cm in diameter. It is brown to blackish-brown or yellow where the outer bark has fallen off. The apex may have stem scars. When the rhizome and root are subcylindrical, it may bear stems and remains of leaf sheaths, with a subconical root longitundinally wrinkled and lenticellate. It may be brown with dense annulations near the rhizome. The texture tends to be fragile and easily broken. It has an odor and a slight taste. In traditional herbal treatments, it is used to relieve pain and rheumatic conditions, for headache with common cold, arthralgia and aching of the back and shoulders. It is generally prepared by eliminating foreign matter, washing clean, softening thoroughly, cutting into thick slices and sun drying.

*Haliotis Diversicolor Reeve* is also known as sea-ear shell. It is an elongate ovoid, tending to grow from 7 to 9 cm long, 5 to 6 cm wide and 2 cm high. The outer surface is typically a dark red with many irregular spiral ribs and fine growth lines. The spire part is small and the shell body large with typically about 30 tubercular protuberances arranged from the apex of the spire part toward the right, each of the last 6–9 or so protuberances with an opening on the same level with the shell surface. The inner surface is smooth, with a pearl-like luster. The shell is relatively thick with a hard texture and is not easily broken. It is odorless and has a slightly salty taste. In traditional herbal treatments, it is used to subdue hyperactivity of the liver, to improve eyesight due to blurred vision from nebula, optic atrophy and night blindness and for headache and dizziness. It is generally prepared by eliminating foreign matter, washing clean, drying and breaking into pieces.

*Pheretima Aspergillum*, known also as Perrier or earthworm is sour in taste. It is considered in traditional herbal treatments as cold in nature and attributive to the liver, spleen and urinary bladder channels. It is a variety of uses traditionally, including to clear away heat and calm the liver, to relieve spasms, for heat syndrome with convulsions, for types of dizziness, headache and convulsion such as epilepsy, to relieve cough and asthma, to alleviate itching such as with eczema and drug rashes, for arthralgia, to promote diuresis, to lower blood pressure, as well as for mumps, skin ulcers and burns. In addition to the above, its pharmacological actions are known to include uses as a sedative and antipyretic.

The herbal components of the present invention can be used in the form of powder or extract extracted by conventional solvents. One or more diluents such as conventional carriers, antioxidants, preservatives, dissolving agents, disintegrators and solvents may be added to the ingredients. The natural substances of the present invention are air-dried and finely ground or extracted by water, vinegar, such as Zheng Jiang vinegar, or any other solvent which can extract active substances from the natural substances at a temperature of from about 25 degrees C to the boiling point of the solvent during a period from about 5 minutes to about 24hours. The solvent from the extract solution may be distilled off to obtain the extract. The extract may be dissolved, for example in water or vinegar or a mixture thereof to form a tea. The tea is best used after 30 minutes or more, preferably after about 12–24 hours for the tea used for soaking, and in other embodiments, preferably after about 24 hours.

When each of the ingredients is used in the extract form, each of the natural substances may be extracted separately or in combination and may be combined and extracted at the same time to obtain the extract. To the powder or extract of natural substances, diluents may be added as carriers.

In one embodiment, for use as a soaking or washing tea, the natural substances may be extracted in combination, in approximately equal parts by weight, using water and vinegar as a solvent. In another embodiment, for use as an ointment, the tea may be concentrated by distillation and diluted for use as an ointment, and combined with conventional bases such as paraffin, oils, and waxes, including beeswax and borneol.

In another embodiment, the tea may be used on or in a substrate, such as a wipe, medicated pad or sponge. In another embodiment, the tea may be contained in or on a substrate contained in a sock, preferably a non-porous sock having individual spaces for one or more toes, like a glove.

EXAMPLE 1

*Angelicae Pubescens Radix* (50 g), *Notopterygium Radix* (30 g) and *Haliotis Diversicolor Reeve* (50 g) are combined and boiled in 25 ounces of water for five minutes, then simmered at 40° C. for 30 minutes to form a liquid extraction. Zheng Jiang Vinegar (3000 g) is added to the extraction to form a tea and the tea is simmered at 40° C. for 20 minutes. The tea is cooled to room temperature for 30 minutes.

Using Example 1, treatment of a tinea infection can be by soaking the affected area, such as a foot, for about 20 minutes each day for a period of about two weeks.

EXAMPLE 2

*Angelicae Pubescens Radix* (50 g), *Notopterygium Radix* (30 g) and *Haliotis Diversicolor Reeve* (50 g) are combined and boiled in 25 ounces of water for five minutes, then cooled to 40° C. for 30 minutes to form an extraction. Zheng Jiang Vinegar (1500 g) is added to the extraction to form a tea and maintained at 40° C. for 20 minutes. The tea was cooled to room temperature for 24 hours. The tea is distilled at 60° C.–70° C. to concentrate the tea. Liquid is removed to form a powder. Borneol (100 g) and beeswax (800 g) are combined with the powder and mixed at 70° C. to form an ointment. The ointment is disinfected in a steam bath at 100° C. for 30 minutes.

Using Example 2, treatment of a tinea infection can be by topical administration of the ointment about twice each day until skin is healed.

EXAMPLE 3

*Angelicae Pubescens Radix* (50 g), *Notopterygium Radix* (30 g) and *Haliotis Diversicolor Reeve* (50 g) are combined and boiled in 25 ounces of water for five minutes, then cooled to 40° C. for 30 minutes to form a liquid extraction. Zheng Jiang Vinegar (1500 g) is added to the extraction to form a tea and maintained at 40° C. for 20 minutes. The tea is cooled to room temperature for 24 hours. Sixty wipes (8 cm×9 cm) are placed into the tea and covered.

Using Example 3, treatment of tinea infection can be by wiping the affected area for approximately 30 seconds.

EXAMPLE 4

*Angelicae Pubescens Radix* (50 g), *Notopterygium Radix* (30 g) and *Haliotis Diversicolor Reeve* (50 g) are combined and boiled in 25 ounces of water for five minutes, then cooled to 40° C. for 30 minutes to form a liquid extraction. Zheng Jiang Vinegar (1500 g) is added to the extraction to form a tea and maintained at 40° C. for 20 minutes. The tea is cooled to room temperature for 24 hours. The sponge material is placed into the tea so the material absorbs the tea. The sponge with tea is placed within a sock.

Using Example 4, treatment for thick nail can be about 60 minutes to obtain the nail-softening effect of the vinegar, while treatment for athlete's foot can be about 20 minutes.

EXAMPLE 5

*Angelicae Pubescens Radix* (50 g), *Notopterygium Radix* (30 g), *Haliotis Diversicolor Reeve* (50 g) and *Pheretima Aspergillum* (30 g) are combined and boiled in 25 ounces of water for five minutes, then simmered at 40° C. for 30 minutes to form a liquid extraction. Zheng Jiang Vinegar (3000 g) is added to the extraction to form a tea. The tea is simmered at 40° C. for 20 minutes. The tea is then cooled to room temperature for 30 minutes.

Using Example 5, treatment of a tinea infection can be by soaking the affected area, such as a foot, for about 20 minutes each day for a period of about two weeks.

EXAMPLE 6

*Angelicae Pubescens Radix, Notopterygium Radix,* and *Haliotis Diversicolor Reeve,* are combined in a 5:3:5 ratio and boiled in water for about five minutes, then simmered at 35–45° C. for 20–40 minutes to form a liquid extraction. Vinegar (3000 g) is added to the extraction to form a tea and the tea is simmered at 35–45° C. for 10–20 minutes. The tea is cooled to room temperature for about 30 minutes.

Using Example 6, treatment of a tinea infection can be by soaking the affected area, such as a foot, for about 20 minutes each day for a period of about two weeks.

Clinical Experiments

Clinical tests were performed on 296 volunteers. The method of medication was topical application of the tea of the present invention. The natural substances were extracted in combination using water and vinegar as solvents. The tea was prepared using 50 g of *Angelica Pubescens Radix,* 30 g *Notopterygium Radix,* and 50 g *Haliotis Diversicolor Reeve* in 25 ounces of water allowed to boil for 5 minutes then simmered at 40 degrees C for 30 minutes. Zheng Jiang vinegar was added in the amount of 3000 g to the tea and simmered at 40 degrees C for 20 minutes, then allowed to cool to room temperature for 24 hours. Treatment was once daily for two weeks.

Of the 296 patients treated in the clinical test, 132 (44.59%) were considered significantly effected, having relief of itching within 3 days, with skin healed in 7 days or fewer and without re-occurrence for at least 13 months. Positively effected patients, having relief of itching in 4–7 days, with skin healed in 8–14 days and without reoccurrence for 7–12 months, numbered 98 (33.11%). Effected cases, having itching disappearing in 8–14 days, with skin healed in 15–21 days and without reoccurrence for 3–6 months numbered 43 (14.53%). Those patients for whom relief of itching required 15 or more days and for whom reoccurrence was seen within 3 months were 23 (7.77%). The total effected cases for this clinical test was 273 (over 92%).

Controlled Study

A controlled study was also performed. The study group was treated with topical application of the tea of the present invention, prepared by the method described above. Of those treated, 84% were effected, having relief of itching within 15 days, with skin healed in 21 days or fewer and no reoccurrence for at least 3 months, as above. The control group received no antifungal medication. Of the control group, 17% had relief of itching within 15 days, with skin healed within 21 days and without reoccurrence for at least 3 months.

Case Study 1

A patient was treated by wearing a glove containing a spongy material with the herbal composition, prepared by the method described above. Treatment was for 3 hours each day for 10 days. Relief of itching occurred after first treatment. Within 3 days, the skin healed, peeling stopped, the skin was smoother, and the affected nail softened. Within 2 months, a normal nail grew in and patient was without re-occurrence for at least 12 months. Ranges of amounts of the ingredients in the combination and the tea can be varied. The following examples are intended to be exemplary only.

EXAMPLE 7

*Angelicae Pubescentis Radix* 30–40%
*Notopterygium Radix* 17–25%
*Haliotis Diversicolor Reeve* 30–40%

EXAMPLE 8

*Angelicae Pubescentis Radix* 30–40%
*Notopterygium Radix* 17–25%
*Haliotis Diversicolor Reeve* 30–40%
*Pheretima Aspergillum* 17–25%

In addition to the above ingredients, the herbal composition may further comprise an acid, such as vinegar or lemon juice which in some cases will have the added benefit of softening the damaged tissue, particularly in the case of tinea unguum, sometimes known as "thick nail." The acid may be added in the range of about 1,000 g–4,000 g.

Various skin treatment products may be fabricated by combining a substrate 100, such as a wipe or sponge, with the herbal composition 110 of the present invention. For convenience, particularly in traveling when treatment is most difficult, the substrate and herbal composition may be housed in a container 120 for bringing the substrate 100 and the herbal composition 110 into contact with each other, such as a dispenser. The wipes 130 are particularly good for preventing the progress of the infection when travel is necessary during the treatment period.

In addition to travel, modern life has many demands on limited time. Treatment, even for a few minutes a day, may be shortened in favor of other activities. Inadequate treatment, however, may unnecessarily prolong the infection and the discomfort associated with it. An extremity covering product, such as a glove 200, sock 300, or digit-covering 400 can be particularly beneficial for treatment as it permits the patient to continue with other activities during the treatment time. For example, a wearable material 210, such as a glove made of cloth, leather or rubber that is lined or partially lined with a substrate 100 that is a porous material, such as a sponge, containing the herbal composition 110 can be easily and conveniently worn for treatment of thick nail. Likewise, a sock 300 that is lined or partially lined with a substrate 100 of a spongy material containing the herbal composition 110 can be worn as an effective treatment for athlete's foot. Likewise, the spongy material may be used separably from the sock or other extremity covering, such as an inner sole device. For infections that are limited to a single digit—a toe or a finger or thumb—a covering for the single digit 400 is fabricated and lined or partially lined with a substrate 100 that is a porous material containing the herbal composition 110 of the present invention.

The invention being thus described, it will be apparent to one skilled in the art that the same may be varied in many ways. Such variations are not to be regarded as a departure from the spirit and scope of the invention, and all such modifications as would be apparent to one skilled in the art are intended to be included in the scope of the following claims.

What is claimed is:

1. An herbal composition comprising *Angelicae Pubescentis Radix*, *Notopterygium Radix* and *Haliotis Diversicolor Reeve*.

2. An herbal composition in accordance with claim 1, wherein *Angelicae Pubescentis Radix*, *Notopterygium Radix* and *Haliotis Diversicolor Reeve* are each provided in an amount effective for the treatment of tinea infection.

3. An herbal composition in accordance with claim 2, wherein *Angelicae Pubescentis Radix* is in an amount approximately 30–40% (dry weight basis) of the combination; *Notopterygium Radix* is in an amount approximately 17–25% (dry weight basis) of the combination; and is *Haliotis Diversicolor Reeve* is in an amount approximately 30–40% (dry weight basis) of the combination.

4. An herbal composition in accordance with claim 2, wherein *Angelicae Pubescentis Radix*, *Notopterygium Radix* and *Haliotis Diversicolor Reeve* are present in a ratio of 5:3:5 dry weight.

5. An herbal composition in accordance with claim 2, further comprising *Pheretima Aspergillum* in an amount approximately 17–25% (dry weight basis) of the combination.

6. An herbal composition in accordance with claim 5, wherein *Angelicae Pubescentis Radix*, *Notopterygium Radix* and *Haliotis Diversicolor Reeve* and *Pheretima Aspergillum* are present in a ratio of 5:3:5:3 dry weight.

7. An herbal composition in accordance with claim 1, further comprising an acid.

8. An herbal composition in accordance with claim 7, wherein each component is provided in an amount effective for the treatment of tinea infection.

9. An herbal composition in accordance with claim 8, wherein the acid is in the form of vinegar.

10. An herbal composition in accordance with claim 7, wherein each component is provided in an amount effective for the treatment of tinea unguum.

11. An herbal composition in accordance with claim 7, wherein each component is provided in an amount effective for the treatment of tinea pedis.

12. An herbal composition in accordance with claim 7, wherein each component is provided in an amount effective for the treatment of tinea corporis.

13. An herbal composition in accordance with claim 7, wherein each component is provided in an amount effective for the treatment of tinea capitis.

14. An herbal composition in accordance with claim 7, wherein each component is provided in an amount effective for the treatment of tinea cruris.

15. An herbal composition in accordance with claim 7, wherein each component is provided in an amount effective for the treatment of tinea versicolor.

16. An herbal composition in accordance with claim 8, wherein *Angelicae Pubescentis Radix* is in an amount approximately 30–40% (dry weight basis) of the combination before extraction; *Notopterygium Radix* is in an amount approximately 17–25% (dry weight basis) of the combination, *Haliotis Diversicolor Reeve* is in an amount approximately 30–40% (dry weight basis) of the combination, and an acid is in an amount approximately 1,000–3,000 g.

17. An herbal composition in accordance with claim 8, further comprising *Pheretima Aspergillum* in an amount approximately 17–25% (dry weight basis) of the combination before extraction.

18. A skin treatment product comprising a substrate containing An herbal composition in accordance with claim 7.

19. A skin treatment product comprising a substrate, An herbal composition in accordance with claim 7, and a container for bringing the cloth and the herbal composition into contact with each other.

20. An extremity covering product comprising a wearable material, a porous material abutting one side of the wearable material and an herbal composition in accordance with claim 2.

21. An extremity covering product in accordance with claim 20 wherein the wearable material is in a form suitable for wearing on the hand.

22. An extremity covering product in accordance with claim 20 wherein the wearable material is in a form suitable for wearing on the foot.

23. An extremity covering product in accordance with claim 20 wherein the wearable material is in a form suitable for wearing on the digit.

24. An extremity covering product in accordance with claim 20, wherein the herbal composition further comprises an acid.

25. A method of making a composition for treatment of tinea infections comprising combining herbal ingredients *Angelicae Pubescentis Radix*, *Notopterygium Radix* and *Haliotis Diversicolor Reeve* to form a combination;

adding water to the combination;

boiling the combination and water for about 3–7 minutes to form an extraction;

simmering the extraction to about 35° C.–45° C. for about 20–40 minutes;

adding an acid to the extraction to form a tea;

simmering the tea at about 35° C.–45° C. for about 10–20 minutes;

allowing the tea to cool to about 25° C.

26. A method of making a composition for treatment of tinea infections in accordance with claim 25, wherein *Angelicae Pubescentis Radix* is in an amount approximately 30–40% (dry weight basis) of the combination before extraction; *Notopterygium Radix* is in an amount approximately 17–25% (dry weight basis) of the combination before extraction; and is *Haliotis Diversicolor Reeve* is in an amount approximately 30–40% (dry weight basis) of the combination before extraction.

27. A method of making a composition for treatment of tinea infections in accordance with claim 25, wherein *Angelicae Pubescentis Radix*, *Notopterygium Radix* and *Haliotis Diversicolor Reeve* are present in a ratio of 5:3:5 dry weight before extraction.

28. A method of making a composition for treatment of tinea infections in accordance with claim 25, wherein combining herbal ingredients further comprises *Pheretima Aspergillum* in an amount approximately 17–25% (dry weight basis) of the combination before extraction.

29. A method of making a composition for treatment of tinea infections in accordance with claim 25, further comprising distilling the tea at 60° C.–70° C.;

adding a base to form an ointment.

30. A method of making a composition for treatment of tinea infections in accordance with claim 29, wherein the base comprises borneol and beeswax.

31. A method of making a composition for treatment of tinea infections in accordance with claim 29, further comprising disinfecting the ointment.

32. A method of making a composition for treatment of tinea infections in accordance with claim 31, wherein disinfecting the ointment further comprises placing the ointment in a steam bath for 20–40 minutes.

33. A method of treating a patient having a tinea infection comprising topical administration of an herbal composition in accordance with claim 2.

34. A method of treating a patient having a tinea infection comprising topical administration of an herbal composition in accordance with claim 7.

* * * * *